United States Patent
Benson et al.

(10) Patent No.: US 7,695,435 B2
(45) Date of Patent: Apr. 13, 2010

(54) SYSTEM AND METHOD FOR TAGGING AND DETECTING SURGICAL IMPLEMENTS

(76) Inventors: Randall J Benson, 1412 Seacrest Dr., Lummi Island, WA (US) 98262; George P O'Brien, 142 Wren School Rd., Piedmont, SC (US) 29673; Zinovy Y Royzen, 12013 C 12 Ave. NW., Seattle, WA (US) 98177; Thomas S Siegel, 6585 Hill St., Dearborn Heights, MI (US) 48127

( * ) Notice: Subject to any disclaimer, the term of this patent is extended or adjusted under 35 U.S.C. 154(b) by 254 days.

(21) Appl. No.: 11/438,504

(22) Filed: May 22, 2006

(65) Prior Publication Data

US 2006/0270933 A1    Nov. 30, 2006

Related U.S. Application Data

(60) Provisional application No. 60/685,048, filed on May 25, 2005.

(51) Int. Cl.
*A61B 3/16* (2006.01)

(52) U.S. Cl. ........................... 600/404; 600/424

(58) Field of Classification Search ............... 600/424, 600/407; 128/899; 329/370; 340/572.1
See application file for complete search history.

(56) References Cited

U.S. PATENT DOCUMENTS

| | | | | |
|---|---|---|---|---|
| 4,114,601 A * | 9/1978 | Abels | ........................ | 600/20 |
| 6,026,818 A * | 2/2000 | Blair et al. | ................... | 128/899 |
| 6,184,680 B1 * | 2/2001 | Shinoura et al. | ............ | 324/252 |
| 6,690,963 B2 * | 2/2004 | Ben-Haim et al. | .......... | 600/424 |
| 6,983,179 B2 * | 1/2006 | Ben-Haim | ................... | 600/374 |
| 7,020,512 B2 * | 3/2006 | Ritter et al. | ................. | 600/434 |
| 7,301,332 B2 * | 11/2007 | Govari et al. | .......... | 324/207.21 |
| 2003/0120150 A1 * | 6/2003 | Govari | ....................... | 600/424 |
| 2003/0135112 A1 * | 7/2003 | Ritter et al. | ................. | 600/424 |
| 2004/0260174 A1 * | 12/2004 | Keene | ........................ | 600/424 |
| 2005/0024043 A1 * | 2/2005 | Govari | ................... | 324/207.17 |
| 2005/0027192 A1 * | 2/2005 | Govari et al. | ............... | 600/424 |

* cited by examiner

*Primary Examiner*—Long V Le
*Assistant Examiner*—Saurel J Selkin

(57) ABSTRACT

A system and method for detecting a surgical implement retained within a surgically exposed human body cavity, includes a tag adapted to be attached to a surgical implement insertable within a human body cavity, including a means for receiving an electromagnetic signal and converting it into electric signal; and a means to impress said electric signal on the internal human (or an animal) body where said medical product is used; and means to transmit said electromagnetic signal; and a detecting means including reception means for receiving the electric signal from the body and a detector means connected to the reception means for detecting the electric signal. The envelope of the induced RF wave is demodulated, thus allowing the voltage at the output to vary at a significantly lower frequency. In the event such pulses are sensed, a sensory alert is actuated.

10 Claims, 2 Drawing Sheets

SYSTEM AND METHOD FOR TAGGING AND DETECTING SURGICAL IMPLEMENTS

This application claims the benefit of provisional Patent Application U.S. 60/685,048 applied May 25, 2005.

BACKGROUND OF THE INVENTION

This invention relates to detection of tagged objects and devices and particularly objects and devices utilized in body cavities during surgery and most particularly to surgical sponges which are frequently "lost" in such body cavities.

During a surgical procedure, and especially in procedures where the chest or abdomen is open, foreign objects such as surgical sponges, needles and instruments are sometimes misplaced within the patient's body cavity. In general any foreign object left within the body can cause complications, (i.e. infection, pain, mental stress) even death, excepting objects such as clips and sutures that are purposely left as part of a surgical procedure.

Presently there are two surgically acceptable procedures for detection and removal of the foreign objects. Firstly, a count of all objects used in the operation is kept by surgical support staff. Secondly, x-ray detection is used to locate foreign objects.

It is not uncommon however, for object counts to be incorrect, but reported erroneously as correct, because of human error. Furthermore, even x-ray detection is not flawless. Furthermore, and most detrimentally, an x-ray is a time delayed detection method because of the requirement for film development (even with quick developing films). A patient will often be completely sutured closed before x-ray results are obtained, which may indicate the location of a foreign object within the patient. The detection delay may therefore result in the necessity for the surgical team to re-open the patient, thereby increasing the morbidity of the operation.

The prior art is replete with means for the detection of foreign objects (aside from x-ray analysis) which may remain in body cavities following surgery. However, such means have either been prohibitively costly, involve detection devices which are too large to be meaningfully useful (i.e., they often impede utilization of the objects they are intended to locate) or simply do not provide effective detection.

There have been a number of devices described in numerous patents for detection of surgical objects such as surgical sponges, which operate by means of marker or tag systems using electromagnetic, magnetomechanical, electromechanical detection techniques. For example, U.S. Pat. No. 2,740,405, issued to Riordian, describes the use of a radioactive tracer for detection of the foreign objects. This method is however, among other things, subject to problems involving the hazards of storage and disposal of radioactive materials.

In another example of detection devices and methods, U.S. Pat. No. 3,422,816, issued to Robinson et al., teaches a technique wherein sponges are marked with a flexible plastic impregnated with paramagnetic or ferromagnetic powders which are detected by a metal detector. However, this method is limited by the small signals obtainable (making detection unreliable), and the lack of discrimination from other magnetically susceptible metal objects, such as surgical staples, which are intended to remain in the body.

In an improvement over the preceding patent, in U.S. Pat. No. 3,587,583, issued to Greenberg, sponges were marked with magnetized particles whose presence is detectable with magnetodiodes. Nevertheless, such method has also not proven to be practical or reliable.

A spate of patents disclose electronically based signal devices, such as disclosed in U.S. Pat. No. 4,114,601, issued to Ables, which discloses use of a gyromagnetic transponder for marking a sponge. Detection is accomplished by a mixing of two frequencies beating the tag. The method however appears impractical because of transmission loss at its operating frequency of 5 Ghz.

In theory, electronic locators should be ideal for the detection of surgical sponges. However, as a practical matter, it is difficult to make a small tag element with sufficient signal strength for reliable detection and at an economic cost. More importantly, the increased size of a tag element often results in a detrimental effect on the utilization of the object it is intended to locate. Thus, surgical sponges, the most common item for which detection is most important, are useful only if they can be deformed for use. However, deformation often distorts large tag elements and small tag elements do not provide sufficient signal strength for detection. A non-deformable large tag is totally counterproductive since it would effectively eliminate the usefulness of a sponge which must be deformed for use.

In U.S. Pat. No. 5,456,718, issued to Szymaitis, a marker is made of non-magnetostrictive or soft magnetic material which will emit known selected harmonic frequencies when exposed to alternating electromagnetic field. However, in practice, this creates a large non-deformable region within the sponge thereby interfering with its function.

In U.S. Pat. No. 5,105,829, issued to Fabian et al, a battery powered marker is disclosed which uses capacitive coupling of radio signal to tissue. In U.S. Pat. No. 5,190,059, Fabian et al teach a battery powered tag used in conjunction with a zone marker housing or field generator. Batteries decreasing reliability of the tags while increasing their cost.

In U.S. Pat. No. 5,057,095, Fabian et al teach marking surgical instruments with three types of resonant markers which produce identifying characteristics when exposed to an alternating magnetic field. First, there is a mangnetomechanical marker. Second, there is a magnetostrictive marker. (Both these devices are however susceptible to pressure and stress making them impractical in an environment, e.g., sponge, requiring compression, with pressure and stress as a function thereof.)

In U.S. Pat. No. 6,366,206 issued to Ishikawa et al., one or more transponders each include a memory containing the corresponding identifying data which is emitted by the respective transponder in response to an electromagnetic signal emitted externally of the transponder.

In U.S. Pat. No. 6,026,818 issued to Blair et al., the system includes a ferrite rod, coil and capacitor. The tag resonates with a radiated signal, in response to the wide band transmission, at its own single non-predetermined frequency.

A very important characteristic absent from many of the prior art expedients is, besides being effective in use, the economics involved. Thus, many of the tags described in the prior art cost well in excess of $0.30 per tag. While this is usually dwarfed by actual surgical costs, it is nevertheless a sufficiently significant amount to cause concern among potential users of sponges with cost of $0.10 per sponge.

As an example of miniature electronic tags, U.S. Pat. No. 4,658,818, issued to Miller et al, discloses the use of a miniature electrical oscillator which is attached to each surgical implement and actuated at the time of surgery. Detection occurs by coupling the oscillation with the patient's tissue. However, the active tagging system has to have a battery lasting the whole duration of the surgery which increasing the complexity, size and cost of the tagging system and decreasing its reliability.

SUMMARY OF THE INVENTION

It is therefore an object of the present invention to provide a method and device suitable for detection of the presence of objects and particularly suitable for use in detection of objects such as surgical sponges and instruments forgotten within the patient's body cavity during surgery, wherein the device comprises detection tags which are sufficiently small, whereby they do not impede use of an object such a surgical sponge or are larger hut flexible, and are reliable in discriminating detection, and yet are economical for widespread use in objects such as sponges.

Figure 1:
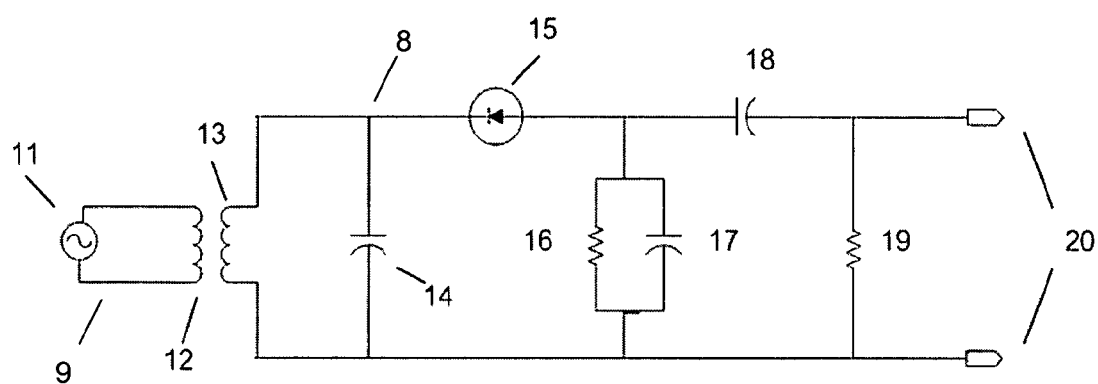
FIG. 1 is an example of an electric circuit of the tag and external means to transmit electromagnetic signal.

The system for detecting a surgical implement (not shown) retained within a human body cavity includes the tag 8 attached to the surgical implement. The tag 8 is inductively coupled from external means for transmission 9. The tag 8 converts received electromagnetic signal into an electric signal. The electric signal is detected by detecting means 10 due to electric conductivity of biological tissue.

DETAILED DESCRIPTION OF THE PREFFERED EMBODIMENT

By reference from Communications Electronics Circuits second edition by J. J. DeFrance Rinehart Press, 1972, page 242 to FIG. 1, an exemplary description is made of a diode detector for the demodulation of electromagnetic waves. Means 9 for transmitting an electromagnetic signal includes an oscillator 11 and a loop antenna, depicted as an inductor 12. While the oscillator in this embodiment operates preferentially at 13.56 MHz, other frequencies may also be used. The tag 8 is attached to a surgical implement (not shown) and adapted to be inserted into a surgically exposed human body cavity includes means for receiving the transmitted electromagnetic signal and converting this electromagnetic signal into an electric signal. The means for receiving the electromagnetic signal is depicted as an inductor 13 which is also preferentially a wire loop antenna that is part of the body resonance detector circuit. The values of this inductor and its corresponding capacitor 14 are selected to resonate at the aforementioned oscillator frequency. The diode 15 conducts only on the positive half-cycle of the resonant circuit, tending to charge capacitor 17 of the resonant tank circuit comprised of capacitor 17 and resistor 16. Values of elements 16 and 17 are chosen so that the discharge time constant is long compared to the period of the RF cycles. The result, as illustrated in FIG. 2, is to demodulate the envelope of the induced RF wave, thus allowing the voltage at output 20 to vary at a significantly lower frequency. In this embodiment, the frequency of modulation or intelligence signal will be preferably, but not limited to, 10 KHz. This intelligence frequency should be chosen so as to optimize the physical size of the components in the body resonance detector circuit. Elements 18 and 19 are respectively the output coupling capacitor and resistor whose values are judiciously selected to remove the alternating current from the envelope, thus leaving only the 10 KHz intelligence electric signal.

Figure 2:
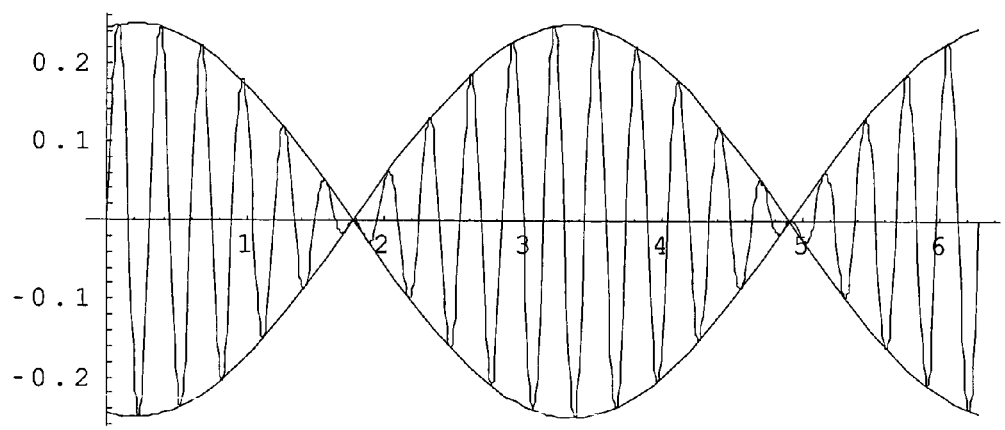
FIG. 2 depicts demodulation of the envelope of the induced RF wave.

Air core inductors values [element 13 in FIG. 1]

| Number of turns | Diameter (inch) | Length (inch) | Inductance (microHenry) |
|---|---|---|---|
| 1 | 4 | 0.04 | 0.22 |
| 1 | 3 | 0.04 | 0.16 |
| 1 | 1 | 0.04 | 0.05 |
| 3 | 1 | 0.1 | 0.49 |

The first assumption of one turn is based on a nominal, unfolded sponge.

The third assumption is a worst case of a triple folded sponge with an original 4 inch single-turn coil becoming effectively a three-turn coil.

Conclusion: We can assume the inductance, L2 will be between 0.16 and 0.49 microHenries Calculation of element 19 FIG. 1 value based on human tissue conductivity. In the following calculation the value of the element 19 equals to the resistance of human tissue across the output electrodes.

Assume electrodes measure 3 mm×3 mm=9 mm ^2

The conductivity of human tissue is nominally 0.3 Siemens/meter. Since resistivity is the reciprocal of the conductivity, the rho or resistivity of human tissue is 3.33 ohms/meter. Therefore, if we assume 2 mm spacing of the electrodes with this resistivity, then:

Resistance=Resistivity×Length/Surface area=Ohms
 Meters×Meters/Meters ^2=Ohms

Element 19 FIG. 1=3.3 ohm meters×(2×10^−3 meters)/(9×10^−3 meters)^2=81.5 Ohms.

To determine the value for Element 18 FIG. 1=t/Element 19 value, where t is the reciprocal of the modulation frequency expressed in hertz.

Summary table of element values for exemplary modulation frequencies:

Element 13 FIG. 1=between 0.16 microH and 0.49 microH
Element 14 FIG. 1=between 1.3 microF and 0.44 microF
Element 16 FIG. 1=50 Ohms (for element 19 value of 82 Ohms)
Element 17 FIG. 1 values :

| 10 Hz | 280 Hz | 1 kHz | 10 kHz |
|---|---|---|---|
| <=400 microF | <=14.4 microF | <=4 microF | <=0.4 microF |

Element 18 FIG. 1 values:

| 10 Hz | 280 Hz | 1 kHz | 10 kHz |
|---|---|---|---|
| 1200 microF | 44 microF | 12.2 microF | 1.2 microF |

Element 19 FIG. 1 depends on the resistivity of human tissue (3.3 Ohm Meters)=81.5 Ohms The tag 8 includes output conducting means to impress an electric signal on the body depicted as output 20 which can be made as electro-conductive pads.

FIG. 1 depicts that inductor 12 (antenna) is electrically connected with the output conducting means.

Figure 3:
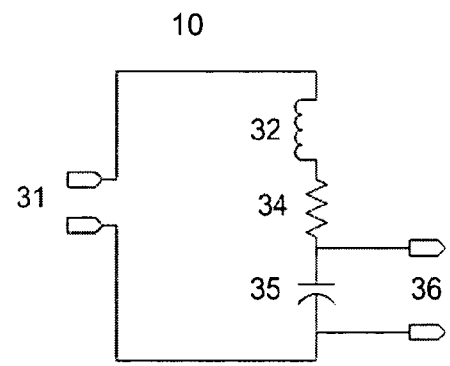
FIG. 3. is an example of a circuit that detects the electric signal (pulses) that has been applied to biological tissue at the output 20 of FIG. 1.

FIG. 3 serves to illustrate an example of a circuit that detects through conduction the low frequency intelligence signal that has been impressed on biological tissue at the output 20 of FIG. 1. example of a resonant The detecting means includes means for receiving the intellingce electric signal from the biological tissue depicted as two conductive pads 31 placed on the biological tissue to receive the input from output 20 of FIG. 1.

In another embodiment, the lower pad of output 20 may be the antenna itself as it is seen as connected in common to the loop.

The values of elements 32, 34, 35 and 36 are chosen so as to pass the modulation frequency from the body resonance circuit described earlier as illustrated in FIG. 1. Exemplary values depending on frequency are:

|  | 10 Hz | 280 Hz | 1 kHz | 10 kHz |
| --- | --- | --- | --- | --- |
| Element 32 (microHenries) | 330 | 330 | 330 | 330 |
| Element 34 (Ohms) | 10 | 10 | 10 | 10 |
| Element 35 (micro Farad) | 767,585 | 980 | 77 | 0.77 |

Other combinations of frequencies and component values may be calculated by anyone of ordinary skill in the art. Values of anticipated output voltage at 36 for input into an instrument such as a voltmeter given a voltage at 31 of 1 millivolt would be:

|  | 10 Hz | 280 Hz | 1 kHz | 10 kHz |
| --- | --- | --- | --- | --- |
| Output 36 (milliVolts) | 0.002 | 0.058 | 0.2 | 2 |

By examination of the component values shown above, the preferred embodiment of 10 kHz modulation frequency allows the selection of more abundant, less expensive and smaller sized elements.

An electrocardiographic device can be used as detector means. An electrocardiographic device is available in the operating room and it is electrically connected to the human body where surgical implements are placed.

Detecting means can be connected (including wireless connection) to the computer located in the operation room.

In another embodiment, the reception means 31 are adapted for electric contact with the human body inside the human body cavity into which is a surgical implement provide with a tag is inserted.

In another embodiment, the reception means 31 are adapted for electric contact with the human body externally of a human body into which a surgical implement provided with a tag is inserted.

In another embodiment, the means 9 to transmit electromagnetic signal is adapted to be located inside the human body cavity into which a surgical implement provided with a tag is inserted.

In another embodiment, the means 9 to transmit electromagnetic signal is adapted to be located externally of a human body into which surgical implement provided with a tag is inserted.

A tag could be used as as X-ray detectable means.

A tag can be attached to X-ray detectable thread to be woven into sponges during their manufacturing.

A tag can be attached to a sponge during or after its manufacturing.

A tag can be woven into sponge, sewn, stapled, glued, etc.

A tag can be attached to a sponge during or after its manufacturing.

A tag can be inserted into a sponge between its layers.

A method for detection of a foreign object used during surgery but not intended to remain in a human body after surgery comprises the steps of:
(a) Providing a foreign object used during surgery with at least one tag,
(b) Transmitting an electromagnetic signal when said detection is needed, for example, during or after the surgery,
(c) Converting said electromagnetic signal into electric signal
(d) Impressing said electric signal on the tissue of the said body,
(e) Electrically connecting detecting means to said body,
(f) Detecting said electric signal conducted by the tissue of the said body.

What is claimed is:

1. A system for detecting a surgical implement retained within a surgically exposed body cavity, the system comprising, in combination:
   (1) means for transmitting a modulated radio frequency (RF) electromagnetic signal;
   (2) a tag adapted to be attached to a surgical implement insertable within a body cavity, and including:
      (a) receiving means for receiving said modulated RF electromagnetic signal and converting it into an electric signal said receiving means including at least one antenna and one capacitor with values chosen for resonating at said RF;
      (b) a diode detector for rectifying and demodulating of said electric signal;
      (c) output means including two electrodes adapted for impressing the modulated frequency electric signal on the internal tissue of the body cavity where said surgical implement is used;
      (d) an output capacitor coupled with said diode detector and said output means; and
      (e) an output resistor coupled with said output capacitor and said output means whose value equals to the resistance of the tissue across said output means; and
   (3) detecting means including:
      (a) reception means for receiving through conduction said electric signal impressed on the tissue by said electrodes including at least two conductive pads adapted for placing on the biological tissue; and
      (b) detector means connected to the reception means for sensing said electric signal.

2. A system as in claim 1 in which said antenna is electrically connected with said output means and adapted to be used as one of electrodes of said output means.

3. A system as in claim 1 in which said receiving means are adapted for electric contact with the body cavity into which is inserted a surgical implement provided with a tag.

4. A system as in claim 1 in which said receiving means are adapted for electric contact with the outside of a body cavity into which is inserted a surgical implement provided with a tag.

5. A system as in claim 1 in which said means for transmitting a modulated electromagnetic signal is adapted to be located inside a human body cavity into which a surgical implement provided with a tag has been inserted.

6. A system as in claim 1 in which said means for transmitting a modulated electromagnetic signal is adapted to be located outside a human body into which a surgical implement provided with a tag has been inserted.

7. A system as in claim 1 in which said detecting means includes an electrocardiographic device.

8. A system as in claim 1 in which said detecting means is connected to a computer located in the operation room.

9. A system as in claim 1 in which the inductance of said antenna range from 0.16 microHenries to 0.49 microHenries.

10. A method for detection of a foreign object used during surgery but not intended to remain in a human body after surgery comprises the steps of:
   (a) Providing a foreign object used during surgery with at least one tag;
   (b) Transmitting an electromagnetic signal of frequency 1 modulated with frequency 2;
   (c) Converting said electromagnetic signal, using the tag, into an electric signal with frequency 2;
   (d) Impressing said electric signal with frequency 2 on the tissue of the said body,
   (e) Electrically connecting detecting means to said body,
   (f) Detecting said electric signal with frequency 2 conducted by the tissue of the said body using said detecting means.

* * * * *